United States Patent [19]

Buschmann et al.

[11] Patent Number: 4,942,244
[45] Date of Patent: Jul. 17, 1990

[54] DIASTEREOMERIC TRIAZOLYL GLYCOL ETHERS-FUNGICIDES AND GROWTH REGULATORS

[75] Inventors: Ernst Buschmann, Ludwigshafen; Linhard Sproesser, Bad Durkheim; Bernd Zeeh; Johann Jung, both of Limburgerhof; Wilhelm Rademacher, Limburgerhof; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 180,690

[22] Filed: Apr. 8, 1988

Related U.S. Application Data

[62] Division of Ser. No. 829,774, Feb. 13, 1986, abandoned.

[30] Foreign Application Priority Data

Feb. 13, 1985 [DE] Fed. Rep. of Germany ....... 3504897

[51] Int. Cl.$^5$ ............................................ C07D 249/08
[52] U.S. Cl. .................................................. 548/268.2
[58] Field of Search ........................ 514/383; 548/262

[56] References Cited

U.S. PATENT DOCUMENTS

| 4,411,687 | 10/1983 | Zeeh et al. | 548/262 |
| 4,436,548 | 3/1984 | Zeeh et al. | 71/76 |
| 4,554,285 | 11/1985 | Zeeh et al. | 548/262 |

FOREIGN PATENT DOCUMENTS

| 015639 | 9/1980 | European Pat. Off. | 548/262 |
| 0019153 | 11/1980 | European Pat. Off. | 548/262 |
| 2102796 | 2/1983 | United Kingdom | 548/262 |

Primary Examiner—Glennon H. Hollrah
Assistant Examiner—Patricia L. Morris
Attorney, Agent, or Firm—Keil & Weinkauf

[57] ABSTRACT

Diastereomers of the formula

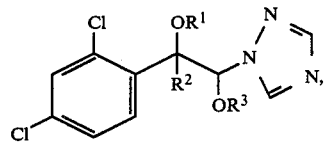

Where $R^1$ is hydrogen, alkyl, alkenyl, alkynyl or benzyl, $R^2$ is a alkyl or alkenyl, $R^3$ is alkyl or benzyl, and the asymmetric centers of the molecular have (a) an RR or SS or (b) an RS or SR configuration, and a process for their preparation and fungicides containing the compounds.

2 Claims, No Drawings

DIASTEREOMERIC TRIAZOLYL GLYCOL ETHERS-FUNGICIDES AND GROWTH REGULATORS

This application is a division of application Ser. No. 829,774, filed on Feb. 13, 1986, now abandoned.

The present invention relates to novel diastereomers of triazolyl glycol ethers, processes for their preparation, and the use of the substances for controlling pathogenic fungi and for regulating plant growth.

It is known that triazolyl glycol ethers possess plant growth-regulating and fungicidal properties (German Laid-Open Applications DOS 2,926,280, DOS 3,047,726 and DOS 3,150,204). The products exhibit good activity but the effect achieved at low application rates is unsatisfactory.

We have found diastereomers of the triazolyl glycol ethers of the formula

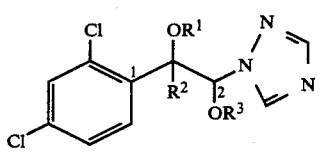

where $R^1$ is hydrogen, alkyl, alkenyl, alkynyl or unsubstituted or substituted benzyl, $R^2$ is alkyl or alkenyl, $R^3$ is alkyl, cycloalkyl or unsubstituted or substituted benzyl, and the asymmetric centers of the molecule, $C_1$ and $C_2$, have (a) an RR or SS or
(b) an RS or SR configuration, which have a good fungicidal and plant growth-regulating action.

Mixtures which contain 80–95% by weight of a diastereomer of the formula I$a$ according to claim 1 and 20–5% by weight of the corresponding diastereomer of the formula I$b$, and mixtures which contain 80–95% by weight of the diastereomer of the formula I$b$ according to claim 1 and 20–5% by weight of the corresponding diastereomer of the formula I$a$ likewise possess good activity.

We have furthermore found that the novel diastereomeric triazolyl glycol ethers of the formula I$a$

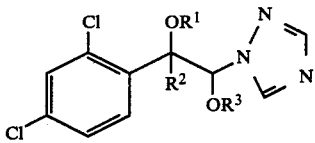

where $R^2$ and $R^3$ have the above meanings, $R^1$ is hydrogen and $C_1$ and $C_2$ have an SS or RR configuration, are obtained from a ketone of the formula II

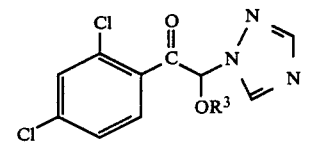

by means of a diastereoselective Grignard reaction, and, if required, the resulting erythro-alcohol compound is converted to an ether of the formula I$a$

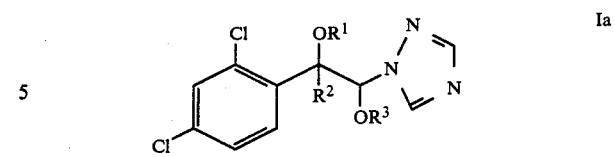

where $R^2$ and $R^3$ have the above meanings, $R^1$ has the above meanings except for hydrogen, and the asymmetric carbon atoms $C_1$ and $C_2$ have an RR or SS configuration. The diastereoselective Grignard reaction is preferably carried out by initially taking a solution of the ketone II and slowly adding the organometallic compound $R^2MgX$ (where X is halogen) to this solution.

We have furthermore found that the novel diastereomeric triazolyl glycol ethers of the formula I$b$

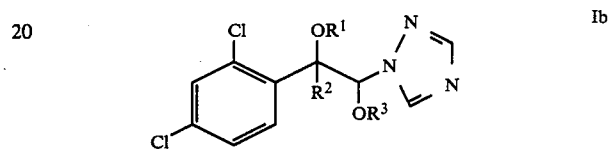

where $R^2$ and $R^3$ have the above meanings, $R^1$ is hydrogen and $C_1$ and $C_2$ have an SR or RS configuration, are obtained from a ketone of the formula

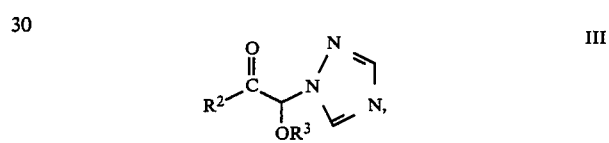

where $R^2$ and $R^3$ have the above meanings, by means of a diastereoselective Grignard reaction, and, if required, the resulting threo-alcohol compound is converted to an ether of the formula I$b$

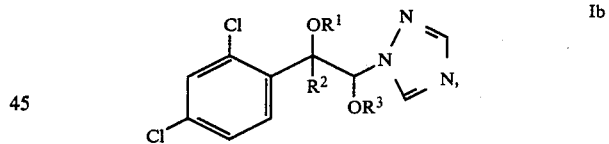

where $R^1$, $R^2$ and $R^3$ have the above meanings, except that $R^1$ cannot be hydrogen, and the asymmetric carbon atoms $C_1$ and $C_2$ have an RS or SR configuration. The diastereoselective Grignard reaction is preferably carried out by initially taking a solution of ketone III and adding the organometallic compound

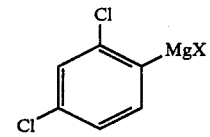

(where X is halogen) slowly to this solution.

In formula I, $R^1$ is preferably hydrogen, alkyl of 1 to 6 carbon atoms, such as methyl, ethyl, n-propyl, isopropyl, n-butyl, isobutyl, 3-methylbutyl or n-pentyl, or is preferably benzyl which is unsubstituted or substituted by halogen, e.g. chlorine, or by $C_1$–$C_4$-alkyl or trifluoromethyl, such as benzyl, 4-chlorobenzyl, 2,4-dichlorobenzyl, 4-fluorobenzyl, 4-methylbenzyl or 4-CF₃-benzyl, or is preferably alkenyl of 2 to 4 carbon atoms, such as allyl, crotyl or propargyl.

$R^2$ is preferably alkyl of 1 to 4 carbon atoms, such as methyl, ethyl or n-propyl, or alkenyl of 2 or 3 carbon atoms, such as vinyl or allyl.

$R^3$ is preferably alkyl of 1 to 6 carbon atoms, such as methyl, ethyl, n-propyl, isopropyl, n-butyl, isobutyl, 3-methylbutyl, n-pentyl or cyclohexyl, or methylcyclohexyl, or is preferably benzyl which is unsubstituted or substituted by halogen, e.g. chlorine, such as benzyl, 4-chlorobenzyl, 2,4-dichlorobenzyl or 4-fluorobenzyl.

The novel erythro-triazolyl glycol ethers of the formula Ia

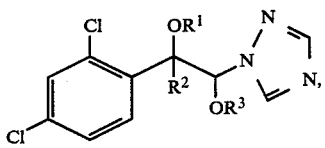

where $R^1$ is alkyl, alkenyl, alkynyl or unsubstituted or substituted benzyl, $R^2$ and $R^3$ have the above meanings and $C_1$ and $C_2$ have an RR or SS configuration, are obtained by substitution at the OH group of the corresponding alcohol of the formula Ia

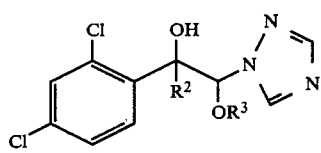

where $R^2$ and $R^3$ have the above meanings and $C_1$ and $C_2$ have an RR or SS configuration, with a halogen compound $R^1X$, where X is Cl, Br or I, in the presence of an acid acceptor, e.g. potassium tert.-butylate or NaH, in a solvent, e.g. dimethylformaldehyde or dimethyl sulfoxide. The erythro configuration is retained in this reaction.

The erythro-alcohols Ia are preferably prepared from a ketone of the formula II

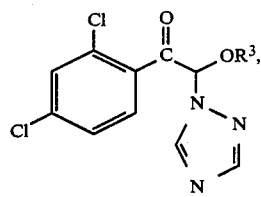

where $R^3$ has the above meanings, by a method in which the ketone II is dissolved in an organic solvent, for example an ether, such as di-n-butyl ether, methyl tert.-butyl ether or diethyl ether, an aromatic hydrocarbon, e.g. toluene, or tetrahydrofuran, this solution is initially taken, and a suspension of a Grignard compound of the formula $R^2MgX$, where $R^2$ has the above meanings and X is Cl, Br or I, in tetrahydrofuran or in an ether, e.g. diethyl ether, di-n-butyl ether or methyl tert.-butyl ether, is slowly added, for example dropwise, to the initially taken solution at from −10° to +40° C., for example at 0° C. (cooling with ice). Surprisingly, the erythrodiastereomer Ia is preferentially formed in this procedure. On the other hand, the process described in DE 2 926 280 leads to undesirable erythro/threo mixtures. Some of the starting compounds of the formula II are described in DE 29 26 280 and can be prepared by the reaction methods stated therein.

The novel threo-triazolyl glycol ethers of the formula Ib

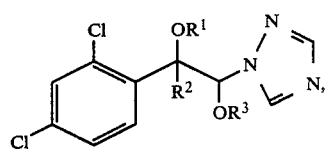

where $R^1$, $R^2$ and $R^3$ have the above meanings, except that $R^1$ cannot be hydrogen, and $C_1$ and $C_2$ have an RS or SR configuration, are obtained by substitution at the OH group of the corresponding alcohol of the formula Ib

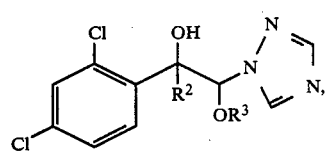

where $R^2$ and $R^3$ have the above meanings and $C_1$ and $C_2$ have an RS or SR configuration, with a halogen compound $R^1X$, where X is Cl, Br or I, in the presence of an acid acceptor, e.g. potassium tert.-butylate or NaH, in a solvent, e.g. dimethylformamide or dimethyl sulfoxide. The threo configuration is retained in this reaction.

The threo alcohols of the formula Ib are preferably prepared from a ketone of the formula III

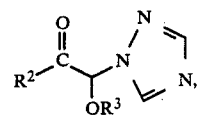

where $R^2$ and $R^3$ have the above meanings, by a method in which the ketone III is dissolved in an organic solvent, for example an ether, e.g. di-n-butyl ether, methyl tert.-butyl ether or diethyl ether, an aromatic hydrocarbon, e.g. toluene, or tetrahydrofuran, this solution is initially taken, and a suspension of a Grignard compound of the formula

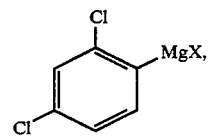

where X is Br or I, in tetrahydrofuran or an ether, e.g. diethyl ether, di-n-butyl ether or methyl tert.-butyl ether, is slowly added, for example dropwise, to the initially taken solution at from −10° to +40° C., for example at 0° C. (cooling with ice). Surprisingly, the threo diastereomer Ib is preferentially formed in this procedure. The process described in DE 2 926 280 leads to undesirable threo/erythro mixtures.

Some of the starting compounds of the formula III are described in DE 2 926 280 and can be prepared by the reaction methods stated therein.

The Examples which follow illustrate the preparation of the novel diastereomers of the formula I.

EXAMPLE 1

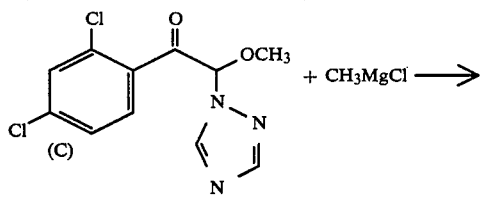

(C)

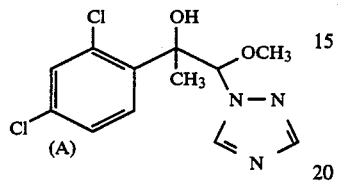

(A)

134 ml of a 1.5 molar solution of CH₃MgCl in tetrahydrofuran were added dropwise to a solution of 28.6 g of ketone (C) in 200 ml of tetrahydrofuran. The mixture was heated for 2 hours at 50° C., left to cool, hydrolyzed with saturated NH₄Cl solution and extracted with ether. The ether extract was dried over Na₂SO₄ and evaporated down. The NMR spectrum of the resulting product showed that the major part of this product was the erythro-diastereomer (δ values (CDCl₃): CH₃COH: 1.9, CHOCH₃: 6.4) in addition to a small amount of ketone (C) and about 5% by weight of the threo-diastereomer (δ values (CDCl₃): CH₃COH: 1.4, CHOCH₃: 6.5). Recrystallization from toluene gave 21 g of alcohol A as the pure erythro-diastereomer (compound No. 1) of melting point 138° C.

EXAMPLE 2

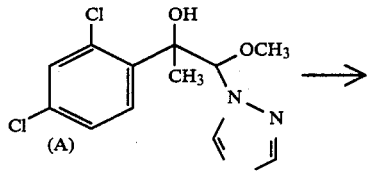

(A)

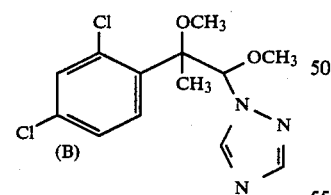

(B)

3.6 g of NaH (80% strength suspension in paraffin) were added a little at a time to a solution of 30 g of alcohol (A) and 17 g of CH₃I in 390 ml of diethyl ether and 110 ml of dimethyl sulfoxide. When the evolution of H₂ was complete, the mixture was refluxed for ½ hour and left to cool, 1.2 l of water were added dropwise and the mixture was extracted with diethyl ether. The organic phase was washed with aqueous Na₂S₂O₃ solution and with water, dried over Na₂SO₄ and evaporated down. Recrystallization from diisopropyl ether gave 21 g of the methyl ether (B) of melting point 92° C. (compound No. 8).

EXAMPLE 3

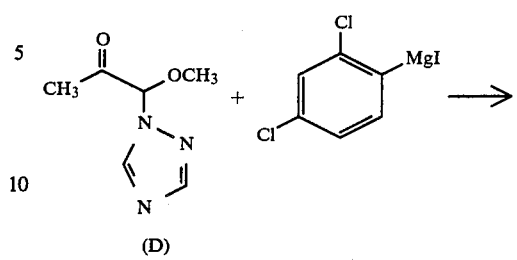

(D)

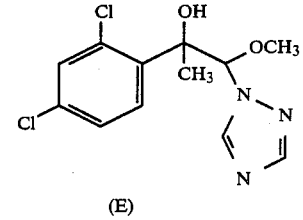

(E)

A Grignard suspension of 0.15 mole of 2,4-dichlorophenylmagnesium iodide in 150 ml of diethyl ether was added dropwise to 0.1 mole of ketone D dissolved in 100 ml of diethyl ether, and the mixture was stirred for 5 hours at room temperature (20° C.), hydrolyzed with 50 g of ice and 50 ml of 25% strength NH₄Cl solution and extracted with ether, and the organic phase was washed with water, dried over Na₂SO₄ and evaporated down. The crude product was stirred with diisopropyl ether, filtered off under suction and washed with petroleum ether. 7.5 g of alcohol E, the pure threo-isomer of melting point 134° C., were obtained (compound No. 14).

The compounds below were obtained in a similar manner.

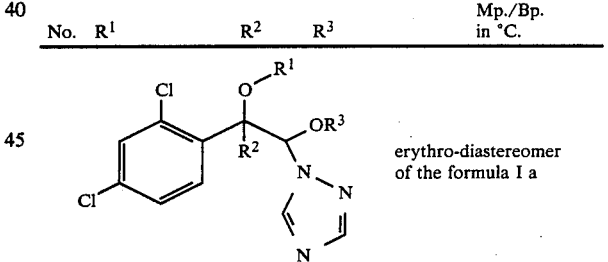

erythro-diastereomer of the formula I a

| No. | R¹ | R² | R³ | Mp./Bp. in °C. |
|---|---|---|---|---|
| 1 | H | CH₃ | CH₃ | 138° |
| 2 | H | C₂H₅ | CH₃ | 130° |
| 3 | H | CH₃ | C₂H₅ | 147° |
| 4 | H | CH₃ | n-C₃H₇ | 97° |
| 5 | H | CH₃ | n-C₄H₉ | |
| 6 | H | CH₃ | isobutyl | |
| 7 | H | CH₃ | n-pentyl | 105° |
| 8 | CH₃ | CH₃ | CH₃ | 92° |
| 9 | C₂H₅ | CH₃ | CH₃ | 90° |
| 10 | allyl | CH₃ | CH₃ | 58° |
| 11 | 2,4-Cl₂-benzyl | CH₃ | CH₃ | 141° |
| 12 | CH₃ | CH₃ | n-butyl | resir. |
| 13 | propargyl | CH₃ | C₂H₅ | 114° |
| 14 | propargyl | CH₃ | CH₃ | 120° |
| 15 | H | Vinyl | CH₃ | 141° |
| 16 | H | CH₃ | benzyl | 162° |
| 17 | H | CH₃ | CH₂-Cyclohexyl | resin |
| 18 | allyl | CH₃ | n-propyl | 174°/0.4 mbar |
| 19 | CH₃ | CH₃ | C₂H₅ | 64° |
| 20 | CH₃ | CH₃ | iso-pentyl | 86° |

-continued

| No. | R¹ | R² | R³ | Mp./Bp. in °C. |
|---|---|---|---|---| threo-diastereomer of the formula I b

[structure: 2,4-dichlorophenyl group attached to CH(R²)–C(OR¹)(OR³)–N linked to 1,2,4-triazole]

| No. | R¹ | R² | R³ | Mp./Bp. in °C. |
|---|---|---|---|---|
| 1.1 | CH₃ | CH₃ | n-butyl | 160–163°/0.3 mbar |
| 1.2 | H | CH₃ | n-propyl | 130° |
| 1.3 | H | CH₃ | C₂H₅ | 103° |
| 1.4 | H | CH₃ | CH₃ | 134° |
| 1.5 | CH₃ | CH₃ | C₂H₅ | 70° |
| 1.6 | H | CH₃ | n-butyl | 96° |
| 1.7 | H | CH₃ | CH₂-cyclohexyl | resin |

In general, the novel compounds exhibit excellent activity against a broad spectrum of phytopathogenic fungi, particularly those from the class consisting of the Ascomycetes and Basidiomycetes. Some of them possess a systemic action and can be used as foliage and soil fungicides.

The fungicidal compounds are of particular interest for controlling a large number of fungi in various crops or their seeds, in particular wheat, rye, barley, oats, rice, corn, lawns, cotton, soybeans, coffee, sugarcane, fruit and ornamentals in horticulture, in viticulture, and in vegetables, such as cucumbers, beans and the cucurbitaceae.

The novel compounds are particularly useful for controlling the following plant diseases:
  Erysiphe graminis (powdery mildew) in cereals,
  Erysiphe cichoracearum and Sphaerotheca fuliginea in cucurbitaceae,
  Podosphaera leucotricha in apples,
  Uncinula necator in vines,
  Puccinia species in cereals,
  Rhizoctonia species in cotton and lawns,
  Ustilago species in cereals and sugarcane,
  Venturia inaequalis (scab) in apples,
  Septoria nodorum in wheat,
  Botrytis cinerea (gray mold) in strawberries and vines,
  Cercospora arachidicola in peanuts,
  Pseudocercosporella herpotrichoides in wheat and barley,
  Pyricularia oryzae in rice,
  Hemileia vastatrix in coffee,
  Alternaria solani in potatoes and tomatoes,
  Plasmopara viticola in vines and
  Fusarium and Verticillium species in various plants.

The compounds are applied by spraying or dusting the plants with the active ingredients, or treating the seeds of the plants with the active ingredients. Application is effected before or after the plants or seeds become infected with the fungi.

The novel substances can be converted to the conventional formulations, such as solutions, emulsions, suspensions, dusts, powders, pastes and granules. The forms for application depend entirely on the intended uses, but should at all events ensure that the active substance is distributed finely and uniformly. The formulations are produced in a conventional manner, for example by extending the active ingredient with solvents and/or carriers, if necessary with the use of emulsifiers and dispersants. Where water is used as a diluent, it is also possible to use other organic solvents as auxiliary solvents. Suitable assistants for this purpose are essentially solvents such as aromatics (e.g. xylene or benzene), chlorinated aromatics (e.g. chlorobenzenes), paraffins (e.g. oil fractions), alcohols (e.g. methanol or butanol), ketones (e.g. cyclohexanone), amines (e.g. ethanolamine or dimethylformamide) and water; carriers, such as ground natural minerals (e.g. kaolins, clays, talc or chalk) and ground synthetic minerals (e.g. highly disperse silica or silicates); emulsifiers, such as non-ionic and anionic emulsifiers (e.g. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient.

The application rates are from 0.02 to 3 kg/ha of active compound, or higher, depending on the type of effect desired. The novel compounds can also be used for protecting material, inter alia for controlling wood-destroying fungi such as Coniophora puteana and Polystictus versicolor. The novel active ingredients can also be employed as fungicidal components of oily wood preservatives for protecting timber against fungi which discolor wood. These agents are used by treating, for example impregnating or painting, the wood with them.

The agents, or the ready-to-use formulations prepared from them, e.g. solutions, emulsions, suspensions, powders, dusts, pastes or granules, are applied in a conventional manner, for example by spraying, atomizing, dusting, scattering, dressing or watering.

Examples of such formulations are:

I. 90 parts by weight of compound No. 1 are mixed with 10 parts by weight of N-methyl-α-pyrrolidone to give a solution which is suitable for use in the form of very small drops.

II. 20 parts by weight of compound No. 14 are dissolved in a mixture consisting of 80 parts by weight of xylene, 10 parts by weight of the adduct of from 8 to 10 moles of ethylene oxide with 1 mole of oleic acid N-monoethanolamide, 5 parts by weight of calcium dodecylbenzenesulfonate and 5 parts by weight of the adduct of 40 moles of ethylene oxide with 1 mole of castor oil. By pouring the solution into water and finely distributing it therein, an aqueous dispersion is obtained.

III. 20 parts by weight of the compound No. 17 are dissolved in a mixture which consists of 40 parts by weight of cyclohexanone, 30 parts by weight of isobutanol and 20 parts by weight of the adduct of 40 moles of ethylene oxide with 1 mole of castor oil. By pouring the solution into water and finely distributing it therein, an aqueous dispersion is obtained.

IV. 20 parts by weight of the compound No. 4 are dissolved in a mixture which consists of 25 parts by weight of cyclohexanol, 65 parts by weight of a mineral oil fraction boiling within the range from 210° to 280° C. and 10 parts by weight of the adduct of 40 moles of ethylene oxide with 1 mole of castor oil. By pouring the solution into water and finely distributing it therein, an aqueous dispersion is obtained.

V. 80 parts by weight of the compound No. 12 are thoroughly mixed with 3 parts by weight of sodium diisobutylnaphthalene-α-sulfonate, 10 parts by weight of the sodium salt of a ligninsulfonic acid obtained from a sulfite waste liquor, and 7 parts by weight of powdered silica gel, and the mixture is milled in a hammer mill. By finely distributing the mixture in water, a spray liquor is obtained.

VI. 3 parts by weight of the compound No. 19 are mixed thoroughly with 97 parts by weight of finely divided kaolin to give a dusting agent which contains 3% by weight of the active ingredient.

VII. 30 parts by weight of the compound No. 19 are mixed thoroughly with a mixture of 92 parts by weight of powdered silica gel and 8 parts by weight of liquid paraffin, which has been sprayed onto the surface of this silica gel. The resulting formulation of the active ingredient exhibits good adhesion.

VIII. 40 parts by weight of the compound No. 6 are mixed thoroughly with 10 parts by weight of the sodium salt of a phenolsulfonic acid/urea/formaldehyde condensate, 2 parts by weight of silica gel and 48 parts by weight of water to give a stable aqueous dispersion. Dilution with water gives an aqueous dispersion.

IX. 20 parts by weight of the compound No. 20 are mixed thoroughly with 2 parts by weight of calcium dodecylbenzenesulfonate, 8 parts by weight of a fatty alcohol polyglycol ether, 2 parts by weight of the sodium salt of a phenolsulfonic acid/urea/formaldehyde condensate and 68 parts by weight of a paraffinic mineral oil. A stable oily dispersion is obtained.

In these forms for application, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclodecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4N-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as dodecylguanidine acetate,
3-[3-(3,5-dimethyl-2-oxycyclohexyl)-2-hydroxyethyl]-glutarimide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate, 5-methyl-5-vinyl-3-(3,5-dichlorophenyl)-2,4-dioxo-1,3-oxazolidine, 3-[3,5-dichlorophenyl]-5-methyl-5-methoxymethyl-1,3-oxazolidine-2,4-dione, 3-(3,5-dichlorophenyl)-1-isopropylcarbamylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole and 2,4-difluoro-α-(1H-1,2,4-triazol-1-ylmethyl)-benzhydryl alcohol.

USE EXAMPLE 1

Action on wheat mildew

Leaves of pot-grown wheat seedlings of the Frühgold variety were sprayed with aqueous spray liquor containing (dry basis) 80% of active ingredient and 20% of emulsifier, and, 24 hours after the spray coating had dried on, the leaves were dusted with oidia (spores) of wheat mildew (Erysiphe graminis var.tritici). The test plants were then placed in a greenhouse at from 20° to 22° C. and from 75 to 80% relative humidity. After 7 days, the extent of powdery mildew development was determined.

| Evaluation: 0 = no fungal infestation, in steps to 5 = total infestation | | A = slight leaf damage B = moderate leaf damage C = pronounced leaf damage | |
|---|---|---|---|
| | Infestation of the leaves after treatment with ... % strength active ingredient liquor | | |
| Active ingredient | 0.025 | 0.006 | 0.0015 |
| 1 | 0 | 0 | 2 |
| 1.4 | 1A | 3 | 4 |
| 3 | 0 | 0 | 0 |
| 1.3 | 3B | 3–4 | 4 |
| 4 | 0 | 0 | 0 |
| 1.2 | 2 | 2 | 3 |
| 12 | 0 | 0 | 2 |
| 1.1 | 1 | 2 | 3–4 |
| 19 | 0A | 0A | 2 |
| 1.5 | 3 | 3 | 3–4 |
| untreated | | 5 | |

USE EXAMPLE 2

Action on cucumber mildew (curative)

Young cucumber plants of the Chinesische Schlange variety, in the two-leaf stage, were sprayed with an aqueous conidial suspension of cucumber mildew (Erysiphe cichoracearum and Sphaerotheca fuliginea). After 3 days, these plants were sprayed to runoff with an aqueous spray liquor containing (dry basis) 80% of active ingredient and 20% of emulsifier, and placed in a greenhouse at from 20° to 22° C. and 70–80% humidity. 21 days after application of the active ingredient, the extent of fungal infestation was determined.

Assessment:
0 = no fungal infestation, in steps to
5 = total infestation

Infestation of the leaves after treatment with ... % strength

| | active ingredient liquor | |
|---|---|---|
| Active ingredient | 0.0125 | 0.006 |
| 1 | 0 | 0 |
| 1.4 | 1 | 2 |
| 3 | 0 | 0 |
| 1.3 | 3–4 | 4 |
| 12 | 0 | 0 |
| 1.1 | 1 | 2 |
| 19 | 0 | 1 |
| 1.5 | 3 | 3–4 |
| untreated | | 5 |

EXAMPLE 3 OF USE

Action on wheat brown rust

Leaves of pot-grown wheat seedlings of the Frühgold variety were dusted with spores of brown rust (Puccinia recondita). The pots were then placed in a chamber at from 20° to 22° C. and with a high humidity (90–95%) for 24 hours. During this time, the spores germinated, and the germ tubes penetrated into the leaf tissue. The infected plants were then sprayed to runoff with aqueous spray liquors containing (dry basis) 80% of active ingredient and 20% of emulsifier. When the spray coating had dried on, the test plants were placed in a greenhouse at from 20° to 22° C. and from 65 to 70% relative humidity. After 8 days the extent of rust fungi development on the leaves was determined.

| Assessment: 0 = no fungal infestation, in steps to 5 = total infestation | A = slight leaf damage B = moderate leaf damage C = pronounced leaf damage |
|---|---|
| | Infestation of the leaves after treatment with 0.025% strength |
| Active ingredient | active ingredient liquor |
| 1 | 1 |
| 1.4 | 3–4 |
| 3 | 2 |
| 1.3 | 3–4A |
| 4 | 0 |
| 1.2 | 3–4 |
| 12 | 0 |
| 1.1 | 2 |
| 19 | 0A |
| 1.5 | 3–4 |
| untreated | 5 |

EXAMPLE 4 OF USE

Action on apple scab

Young leaves of pot-grown apple seedlings of the Golden Delicious variety were sprayed to runoff with aqueous spray liquor containing (dry basis) 80% of active ingredient and 20% of emulsifier. When the spray coating had dried on, the test plants were sprayed with a spore suspension of apple scab (Venturia inaequalis). The inoculated plants were then placed in a conditioned chamber at from 20° to 22° C. and 95% relative humidity for 10 days. The extent of fungal development on the leaves was then determined.

Assessment:
0 = no fungal infestation, in steps to
5 = total infestation

Infestation of the leaves after treatment with 0.0075% strength

-continued

| Active ingredient | active ingredient liquor |
|---|---|
| 4 | 0 |
| 6 | 0 |
| 20 | 1 |
| 1.2 | 1 |
| untreated | 4–5 |

EXAMPLE 5 OF USE

Action on Botrytis cinerea in paprika

After 4–5 leaves were well developed, paprika seedlings of the Neusiedler Ideal Elite variety were sprayed to runoff with aqueous suspensions containing (dry basis) 80% of active ingredient and 20% of emulsifier. When the spray coating had dried on, the plants were sprayed with a conidial suspension of the fungus Botrytis cinerea and placed in a chamber at 22°–24° C. and with a high humidity. After 5 days the disease had developed on the untreated control plants to such an extent that the resulting leaf necroses covered the predominant part of the leaves.

Assessment:
0 = no fungal infestation, in steps to
5 = total infestation

| Active ingredient | Infestation of the leaves after treatment with 0.05% strength active ingredient liquor |
|---|---|
| 1 | 0 |
| 1.4 | 4 |
| 3 | 1 |
| 4 | 0 |
| 12 | 1 |
| 1.1 | 4 |
| 19 | 1 |
| untreated | 5 |

We claim:
1. A process for the preparation of a diastereomer of the formula Ia

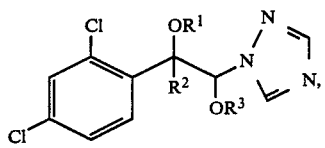

where $R^1$ is hydrogen, alkyl of 1 to 6 carbon atoms, alkenyl of 2 to 4 carbon atoms or unsubstituted or substituted benzyl, $R^2$ is methyl, ethyl or vinyl, $R^3$ is alkyl of 1 to 6 carbon atoms, cyclohexyl, methylcyclohexyl or unsubstituted or substituted benzyl, the substitutions on the $R^1$ and $R^3$ benzyl groups being 1 or 2 halogen, $C_1$–$C_4$-alkyl, trifluoromethyl or $C_2$–$C_4$-alkenyl substituents, and the asymmetric centers of the molecule have an RR or SS configuration, wherein a ketone of the formula II

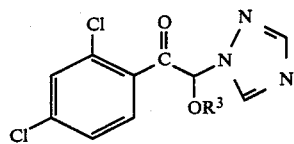

where $R^3$ has the above meanings, is subjected to a diastereoselective Grignard reaction with a compound of the formula $R^2MgX$, where $R^2$ has the meanings given above and X is Cl, Br or I, and, if required, the resulting alcohol compound of the formula Ia

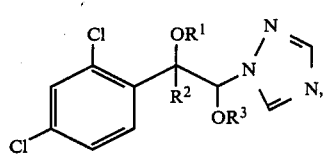

where $R^2$ and $R^3$ have the above meanings, $R^1$ is hydrogen and $C_1$ and $C_2$ have an RR or SS configuration, is converted to an ether of the formula Ia, where $R^1$ has the meanings stated above with the exception of hydrogen.

2. A process for the preparation of the diastereomer of the formula Ib

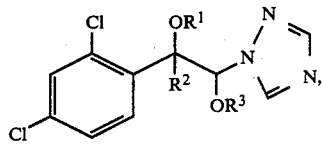

where $R^1$ is hydrogen, alkyl of 1 to 6 carbon atoms, alkenyl of 2 to 4 carbon atoms or unsubstituted or substituted benzyl, $R^2$ is methyl, ethyl or vinyl, $R^3$ is alkyl of 1 to 6 carbon atoms, cyclohexyl, methylcyclohexyl or unsubstituted or substituted benzyl, the substitutions on the $R^1$ and $R^3$ benzyl groups being 1 or 2 halogen, $C_1$–$C_4$-alkyl, trifluoromethyl or $C_2$–$C_4$-alkenyl substituents, and the asymmetric centers of the molecule have an RR or SS configuration, wherein a ketone of the formula III

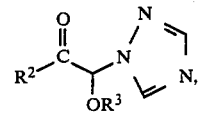

where $R^2$ and $R^3$ have the meanings stated is subjected to a diastereoselective Grignard reaction with a compound of the formula IV

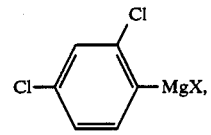

where X is Cl, Br or I, and, if required, the resulting alcohol compound of the formula Ib

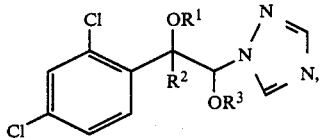

where $R^2$ and $R^3$ have the above meanings, $R^1$ is hydrogen and $C_1$ and $C_2$ have an RS or SR configuration, is converted to an ether of the formula Ib, where $R^1$ has the meanings stated above, with the exception of hydrogen.

* * * * *

UNITED STATES PATENT AND TRADEMARK OFFICE
CERTIFICATE OF CORRECTION

PATENT NO. : 4,942,244

DATED : July 17, 1990

INVENTOR(S) : Ernst BUSCHMANN et al.

It is certified that error appears in the above-identified patent and that said Letters Patent is hereby corrected as shown below:

Abstract of Disclosure

"asymmetric centers of the molecular" should read --asymmetric centers of the molecule--

Signed and Sealed this

Eighth Day of October, 1991

*Attest:*

HARRY F. MANBECK, JR.

*Attesting Officer*     *Commissioner of Patents and Trademarks*